United States Patent

Goumont et al.

[11] Patent Number: 6,024,501
[45] Date of Patent: Feb. 15, 2000

[54] METHOD FOR CONTROLLING THE ACTIVITY OF AN INORGANIC DEVELOPMENT COMPOSITION

[75] Inventors: Claude G. Goumont, Germolles; Gérard R. Sirand-Rey, La Vacacière; Alain André Charret, Chalon sur Saone, all of France

[73] Assignee: Eastman Kodak Company, Rochester, N.Y.

[21] Appl. No.: 09/038,576

[22] Filed: Mar. 11, 1998

[30] Foreign Application Priority Data

Mar. 11, 1997 [FR] France ................................. 97 03364

[51] Int. Cl.⁷ ............................. G03D 3/02; G03D 13/00
[52] U.S. Cl. ........................ 396/570; 396/578; 396/626; 396/632
[58] Field of Search .................................. 396/570, 578, 396/626, 632; 430/413, 416; 355/27–29

[56] References Cited

U.S. PATENT DOCUMENTS

| | | | |
|---|---|---|---|
| 5,489,961 | 2/1996 | Burbury et al. | 396/570 |
| 5,656,515 | 8/1997 | Roussilhe et al. | 430/413 |
| 5,686,232 | 11/1997 | Roussilhe et al. | 430/435 |

FOREIGN PATENT DOCUMENTS

| | | |
|---|---|---|
| 733945 | 9/1996 | European Pat. Off. . |
| 4324141 | 3/1995 | Germany . |

Primary Examiner—D. Rutledge
Attorney, Agent, or Firm—J. Lanny Tucker

[57] ABSTRACT

The invention concerns a method for controlling the activity of a development composition which comprises, as a developing agent, an organometallic complex. The method includes measuring the variations in optical density difference of the composition that varies with the degree of oxidation of the organometallic complex. The method also makes it possible to regenerate the development composition by means of an electrolysis current. A device for controlling the activity of the development composition includes two light-emitting diodes of different wavelengths, the light beams of which pass through the development composition, and photodiodes to receive transmitted light.

7 Claims, 4 Drawing Sheets

METHOD FOR CONTROLLING THE ACTIVITY OF AN INORGANIC DEVELOPMENT COMPOSITION

FIELD OF THE INVENTION

The present invention concerns a novel method for controlling the activity, during photographic processing, of a development composition that comprises an organometallic complex as a developing agent. The invention also includes a method of regenerating the development composition, and a device for controlling composition activity.

PRIOR ART

It is known to use, in conventional photographic processing methods, inorganic developers which contain, as a developing agent, a metallic ion which is capable of changing valency in order to be able to reduce the silver ions into metallic silver. The activity of these developing agents can be improved by the presence of chelating agents that are able to form complexes with the metallic ion of higher valency U.S. Pat. No 5,310,631 describes a composition for developing, after exposure, photographic products consisting of selenium-sensitized silver halide emulsions. The development composition contains as a developing agent an organometallic complex comprising a metallic ion capable of changing valency and an organic acid. In particular, the development composition contains a complex of iron (II) or titanium (III) with a polyaminocarboxylic acid such as EDTA or DTPA or their salts.

Such inorganic development compositions constitute a completely reversible oxidoreduction system and can be regenerated by passing an electrolysis current through them. This mechanism is described by T. H. James in *The Theory of the Photographic Process,* 4th edition, Macmillan Publishing Co. Inc., 1977, pages 294–296. U.S. Pat. Nos. 5,310,631 and 5,424,799 also describe such a regeneration method.

If conventional development compositions containing organic developers such as hydroquinone derivatives are compared with inorganic development compositions containing, as a development agent, a metallic ion capable of changing valency, the metallic developers present certain advantages. In particular, the possibility of regenerating this type of development composition makes it possible to have treatments that reduce the maintenance level of the development compositions and minimize the volume of effluents.

For regenerating development baths, it is advantageous to monitor the reducing activity of the development composition, for example in order to be able to adjust the electrolysis current so as to maintain a constant reducing activity.

Conventionally a standard system for measuring the oxidoreduction potential of the development composition is used that makes it possible to control the potential and therefore the reducing activity of the composition. Measurement is made of the oxidoreduction potential that corresponds to the reducing activity of the composition. When a threshold value is reached, the electrolysis current is adjusted in order to re-establish the desired activity value. However, it was found during an experiment carried out on a composition comprising the complex Ti(III)-EDTA oxidized by sodium persulfate, that the measurement of the oxidoreduction potential of the composition varied greatly according to the pH of the composition. In the case of photographic processing solutions, the pH varies greatly during the processing, which makes measurements of the oxidoreduction potential, and therefore the values of the reducing activity of the development composition, unreliable. This phenomenon is depicted in FIG. 1a.

It is already known that the optical density can be measured in order to measure the aging of a development composition. For example, U.S. Pat. No. 5,489,961 describes a method comprising measuring the optical density of a development composition in order to monitor the darkening of the bath over time.

SUMMARY OF THE INVENTION

The present invention makes it possible to monitor the changes in an inorganic development composition while avoiding the problems of the prior art, in particular avoiding the variations in other properties of the composition such as variations in pH.

This invention provides a method of controlling the activity of a development composition which comprises, as a developing agent, an organometallic complex having at least one metallic ion capable of reducing silver ions and at least one organic chelating agent, said composition also having an optical density that varies measurably as a function of the degree of oxidation of the said organometallic complex, said method comprising measuring the optical density difference of said composition related to the variation in the degree of oxidation of said organometallic complex.

This invention also provides a method of regenerating a development composition which comprises, as a developing agent, an organometallic complex having at least one metallic ion capable of reducing silver ions and at least one organic chelating agent, said composition also having an optical density that varies measurably with the degree of oxidation of the said organometallic complex, said method comprising a) measuring the optical density difference of said composition related to the variation in the degree of oxidation of the said organometallic complex, and b) passing an electrolysis current through said composition, starting from a threshold value of optical density difference, thereby regenerating oxidized organometallic complex until the desired oxidation level is obtained.

Further, this invention provides a device for controlling the activity of a development composition which comprises, as a developing agent, an organometallic complex having at least one metallic ion capable of reducing silver ions and at least one organic chelating agent, said composition also having an optical density that varies measurably with the degree of oxidation of the said organometallic complex, said device comprising at least:

two light-emitting diodes of different wavelengths, the light beam of each diode designed to pass through said development composition, and two photodiodes that receive, respectively, the light beam transmitted by each light-emitting diode through said composition.

DETAILED DESCRIPTION OF THE INVENTION

The invention concerns a method for controlling the activity of a development composition which comprises an organometallic complex developing agent. This complex has at least one metallic ion capable of reducing the silver ions and at least one organic chelating agent. The composition has an optical density that varies measurably according to the degree of oxidation of the organometallic complex (namely according to the degree of oxidation of the metallic ion forming the organometallic complex). Thus, the method includes monitoring the optical density difference of the development composition as a function of variations in the degree of oxidation of the complex, thereby making it possible to monitor the reducing activity of the development composition.

Since the monitoring of the reducing activity of the development composition by means of a measurement of the optical density difference is very precise, it is possible to adapt very precisely the electrolysis current which makes it possible to regenerate the said development composition and maintain a practically constant activity.

BRIEF DESCRIPTION OF THE DRAWINGS

In the description which follows, reference will be made to the drawings in which.

Figure 1A:
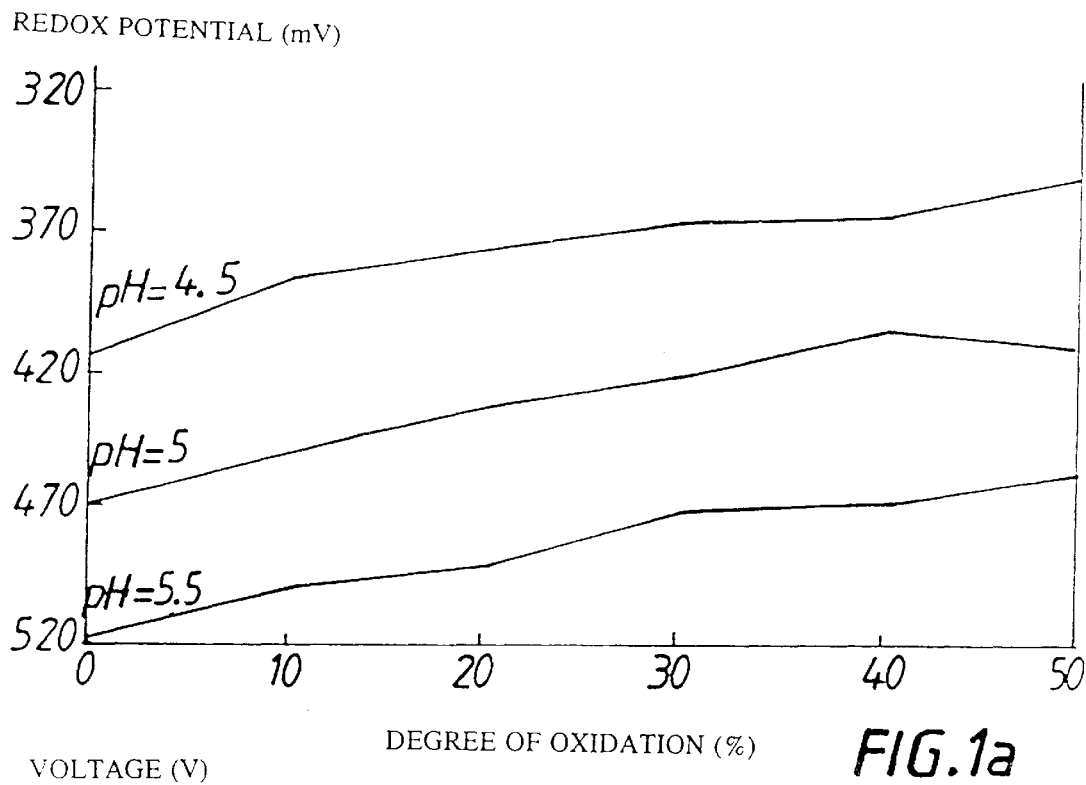
FIG. 1a depicts the influence of the pH on the measurement of the oxidoreduction potential.

According to the invention, the method of monitoring the inorganic development composition comprises measuring an optical density difference of this composition related to the degree of oxidation of the complex. Such a method can be used only for monitoring the reducing activity of an organometallic complex, present in a development composition, which exhibits an appreciable variation in coloring according to the degree of oxidation of the complex.

According to the invention, the inorganic development composition whose activity is monitored preferably comprises a complex of titanium (III) with ethylenediaminetetraacetic acid (EDTA). This Ti(III)-EDTA complex has an intense violet color and is practically colorless in the oxidized state (Ti(IV)-EDTA).

According to the invention, the inorganic development composition can also comprise, in addition to the EDTA chelating agent, a second chelating agent. The second organic chelating agent is preferably a polycarboxylic or aminopolycarboxylic chelating agent. This chelating agent can be nitrilotriacetic acid (NTA), an aminopolycarboxylic acid such as methylene iminodiacetic acid (MIDA), iminodiacetic acid (IDA) or (acetamido)iminodiacetic acid (AIDA), an acid including a heterocyclic ring such as pyridine-2-carboxylic acid (PCA) or pyridine-2,6-carboxylic acid (PDCA), a polycarboxylic acid substituted by one or more hydroxyl groups chosen from among citric acid, tricarballylic acid, tartaric acid, gluconic acid and finally a dicarboxylic aliphatic acid chosen from among malonic, succinic or glutaric acids.

According to a particular embodiment, the second organic chelating agent can have the formula:

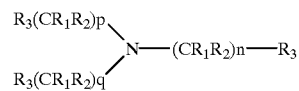

in which $R^1$ and $R^2$ are each separately a hydrogen atom, an alkyl group, substituted or not, 1 to 10 carbon atoms, a hydroxyl group, a hydroxyalkyl group, $R^3$ is a radical chosen from among —COOM in which M is hydrogen or a counter ion such as lithium, sodium or potassium, —CONR$^4$R$^5$ in which $R^4$ and $R^5$ are each separately a hydrogen atom, an alkyl group, substituted or not, 1 to 10 carbon atoms, n, p and q are 1, 2 or 3.

In the context of the invention, variations in coloring as a function of the degree of oxidation of the organometallic complex making it possible to use the monitoring method which will be described subsequently must be significant. According to a particular embodiment, when the complex Ti-EDTA is used, the EDTA represents at least 25% by weight of the total necessary quantity of chelating agent.

The method used for measuring the optical density includes sending a light beam which passes through the composition and measuring the transmission of the light beam through the composition.

According to one embodiment, the composition is circulated in a thin flow cell which is chosen according to the complex. Such a method makes it possible to carry out measurements continuously.

During the development of the photographic films, the organometallic complex will change from a reduced form (Ti(III)-EDTA) to an oxidized form (Ti(IV)-EDTA), reducing, by oxidoreduction reaction, the silver ions (Ag$^+$) to metallic silver (Ag). The reduction in the quantity of organometallic complex in reduced form gives rise to a reduction in the coloring of the composition containing the organometallic complex, which increases the intensity of light transmitted through the composition.

It has been found that, if a single wavelength is chosen to illuminate the composition, the absorption does not vary linearly as a function of the degree of oxidation of the organometallic complex. This phenomenon, shown on curve 3b, is explained by the fact that the optical density of the composition varies not only according to the degree of oxidation of the organometallic complex but also according to the presence of other compounds in the composition and according to the presence of impurities which have appeared over time.

In the context of the present invention, variations in optical density of the composition which are not related to the variation in the degree of oxidation of the organometallic complex are eliminated by using a device consisting of two light-emitting diodes which illuminate the composition, each associated with two photodiodes which receive the light transmitted respectively by each light-emitting diode through the composition. Each photodiode emits a current which is substantially proportional to the optical transmission of the composition.

The device of the invention is a device for controlling the activity of a development composition which comprises, as a developing agent, an organometallic complex comprising of at least one metallic ion capable of reducing the silver ions and at least one organic chelating agent, the organometallic complex being such that the optical density of the composition varies measurably according to the degree of oxidation of the said complex; the device comprising at least two light-emitting diodes of different wavelengths, the light beam of each diode designed to pass through the development composition, two photodiodes that receive respectively the light beam transmitted by each light-emitting diode through the composition.

The device comprises a first light-emitting diode which emits a light with a wavelength corresponding substantially to the maximum absorption value of the absorption spectrum of the complex in the solution used, a second light-emitting diode which emits a light with a wavelength which does not correspond to the maximum absorption value of the absorption spectrum of the complex used, so that the light transmitted to the corresponding photodiode varies according to the presence of other compounds in the composition and/or according to the presence of impurities.

Figure 2:
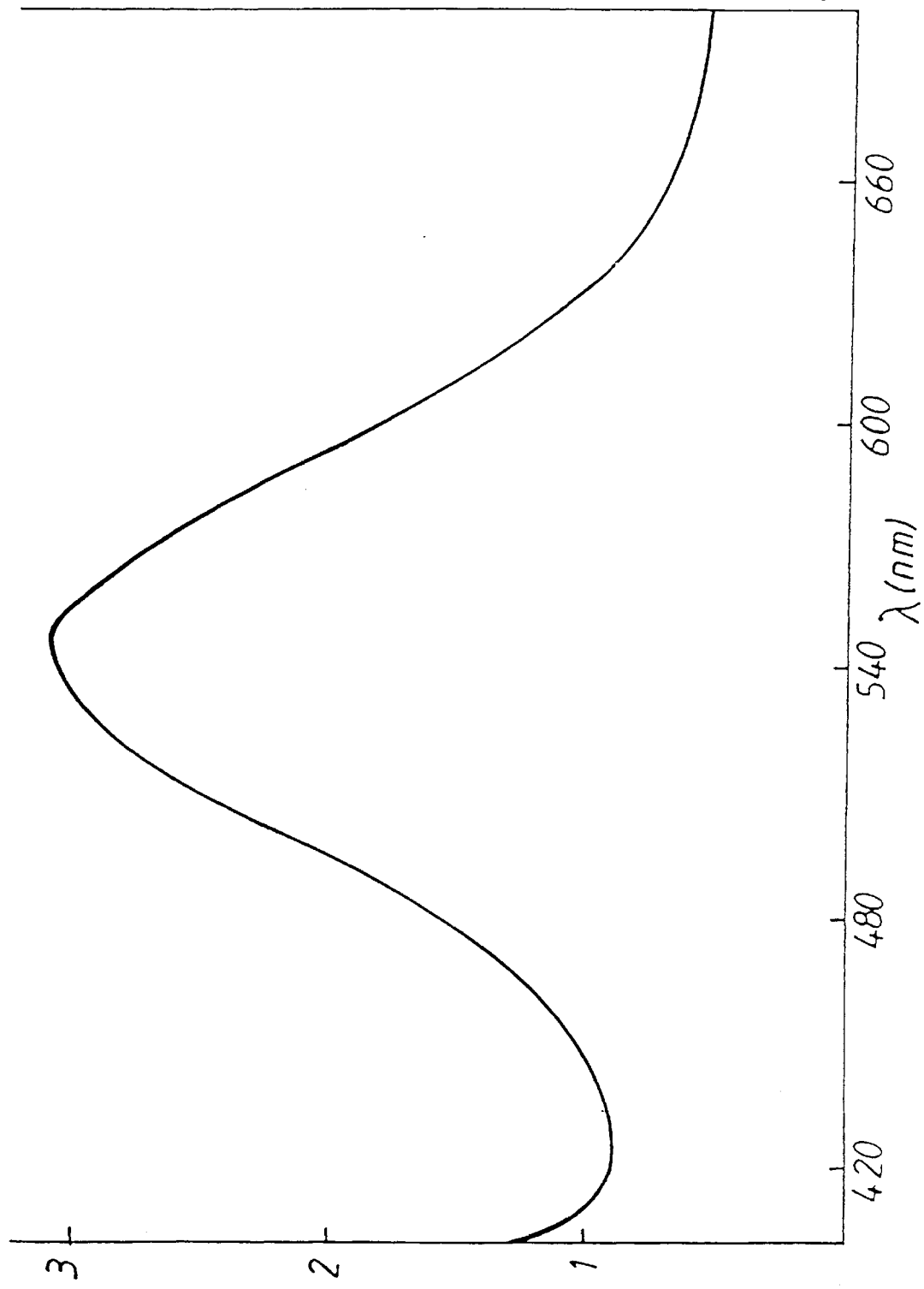
FIG. 2 depicts the absorption spectrum of the organometallic complex Ti(III)-EDTA.
Figure 3:
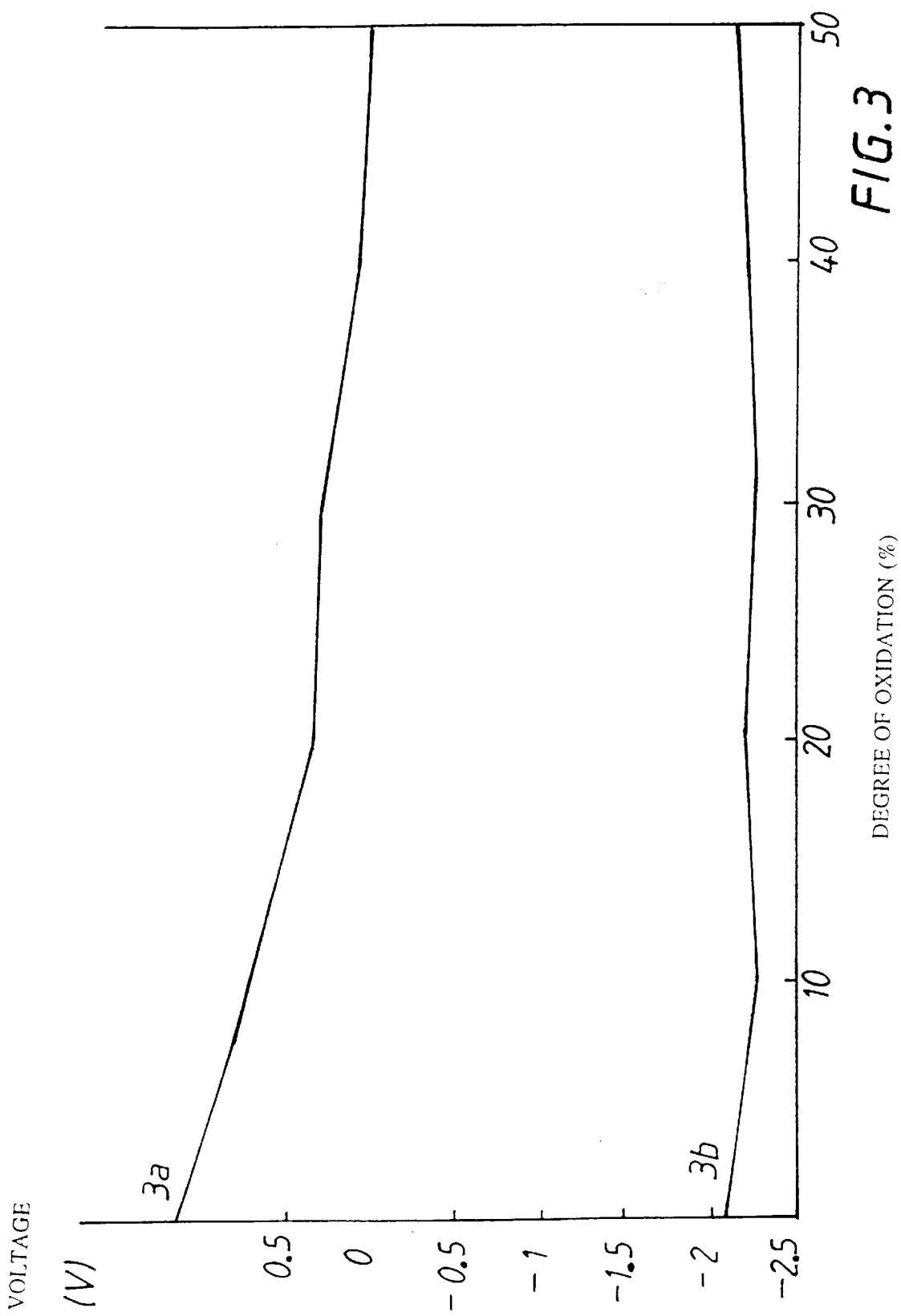
FIG. 3 depicts an example of the monitoring of a voltage, proportional to the optical density, according to the degree of oxidation of the composition.

When the Ti(III)-EDTA complex is used, the absorption spectrum corresponding to this complex, which is depicted in FIG. 2, shows that the first light-emitting diode which must be used emits a light with a wavelength lying between 550 and 560 nm, and preferably 555 nm. The second light-emitting diode which must be chosen emits at a wavelength lying between 450 and 480 nm, and preferably 470 nm.

Thus the optical density difference between the first and second photodiode is measured throughout the reaction. A variation in this difference is solely due to a variation in the optical density related to the degree of oxidation of the complex itself.

Curve 3a shows clearly that the relationship between the optical density difference measured and the degree of oxidation is a bijective function, namely that a single degree of oxidation of the complex corresponds to one optical density difference value, and vice versa.

Figure 4:
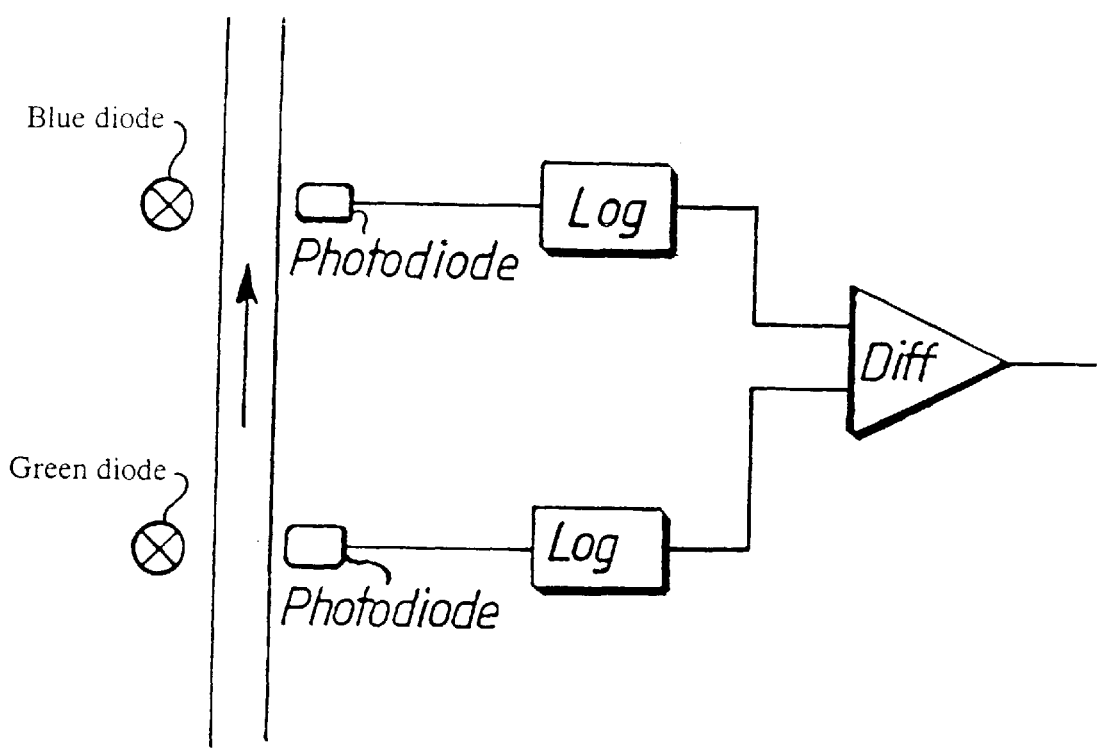
FIG. 4 depicts an electrical diagram for implementing the method.

If reference is made to the diagram in FIG. 4, an electrical system used for making the measurements can be seen. Each photodiode receives respectively the light intensity emitted by each light-emitting diode. The photodiodes used are preferably conventional silicon photodiodes which deliver a current intensity proportional to the quantity of light which they receive. The current intensity of each photodiode is proportional to the optical transmission of the composition. The current emitted by each photodiode is transmitted respectively to two logarithmic amplifiers whose output voltages are proportional to the optical density of the composition. The two outputs of the logarithmic amplifiers are connected to a differential amplifier. The output voltage of the differential amplifier is proportional to the optical density difference measured by each photodiode.

According to the invention, a third light-emitting diode can be used, emitting a wavelength corresponding to another part of the absorption spectrum. This third light-emitting diode, associated with a third photodiode, can make it possible to eliminate variations in optical density due to other interference.

For example, in the case of the Ti-EDTA complex, a light-emitting diode can be adopted which emits a red light.

By measuring the optical density of a developer bath during the processing of photographic products, the reducing activity of the developing agent of the bath is monitored. When the activity reaches a previously fixed threshold value, the electrolysis current is adjusted to re-establish the desired activity value.

A standard oxidoreduction potential control system can be used conjointly with the optical density measurement system which has just been described. It makes it possible to detect any malfunctioning of the optical density measurement system.

EXAMPLE 1 (COMPARATIVE)

The development composition whose reducing activity is to be monitored comprises:

0.4 M of EDTA 0.2 M of $TiCl_3$

A standard system is used for measuring the oxidoreduction potential of the development composition.

The developer bath is oxidized by adding, in increments, 12% sodium persulfate.

The oxidoreduction potential measurements are made for compositions whose pH has been modified. The redox potential measurements are set out in the following table:

| DEGREE OF OXIDATION | REDOX POTENTIAL in mV | | |
|---|---|---|---|
| in % | pH = 4.5 | pH = 5 | pH = 5.5 |
| 0 | −414 | −470 | −518 |
| 10 | −386 | −450 | −500 |
| 20 | −375 | −433 | −492 |
| 30 | −365 | −422 | −472 |
| 40 | −363 | −405 | −469 |
| 50 | −347 | −410 | −458 |

These measurements are set out in the graph in FIG. 1a.

It is found that the redox potential measured for the same value of degree of oxidation varies appreciably with the pH of the composition. This method therefore does not make it possible to monitor the reducing activity of the development composition with precision.

EXAMPLE 2 (COMPARATIVE)

The reducing activity of the same compositions as in Example 1 is monitored.

According to the absorption spectrum of the Ti(III)-EDTA complex, a source of light for illuminating the composition is chosen which is a green light-emitting diode emitting a wavelength of 555 nm (HBG5066X STANLEY®).

A photodiode receives the light transmitted through the composition and emits a current proportional to the optical transmission of the said composition.

The voltage at the terminals of the photodiode is measured for each of the compositions. These measurements are set out in the following table:

| DEGREE OF OXIDATION | VOLTAGE (GREEN) in mV | | |
|---|---|---|---|
| in % | pH = 4.5 | pH = 5 | pH = 5.5 |
| 0 | −2.09 | −2.09 | −2.19 |
| 10 | −2.30 | −2.27 | −2.32 |
| 20 | −2.19 | −2.23 | −2.25 |
| 30 | −2.27 | −2.33 | −2.34 |
| 40 | −2.20 | −2.27 | −2.24 |
| 50 | −2.14 | −2.12 | −2.15 |

The voltage values measured for the composition with a pH of 4.5 are set out on curve 3b.

It is found this time that the voltage values measured do not vary as a function of the pH of the composition. Nevertheless, several values of degree of oxidation correspond to a measured voltage value, namely of optical density of the composition. The use of a single light-emitting diode/photodiode system therefore does not make it possible to monitor the reducing activity of the composition correctly.

EXAMPLE 3

The reducing activity of the same compositions as in Example 1 is monitored.

According to the absorption spectrum of the Ti(III)-EDTA complex, the device used for implementing the method according to the invention comprises:

a first green light-emitting diode which emits at a wavelength of 555 nm (HBG5066X STANLEY®)

a second, blue light-emitting diode emits at a wavelength of 470 nm (L200CWB5-3V/50 LEDTRONICS®)

two photodiodes (BPW34 SIEMENS®)

two logarithmic amplifiers (757P ANALOG DEVICES®)

a differential amplifier (OPA128 BURR BROWN®).

The two photodiodes receive respectively the light intensity emitted by each light-emitting diode. The current emitted by each photodiode is transmitted respectively to two logarithmic amplifiers whose output voltages are proportional to the optical density of the composition. The two outputs of the logarithmic amplifiers are connected to a differential amplifier. The output voltage of the differential amplifier is proportional to the optical density difference measured by each photodiode.

The photographic processing is simulated by a chemical reaction which makes it possible to control the value of the oxidation rate of the Ti(III)-EDTA complex.

Using the device described previously, a measurement is made of the optical density difference between the outputs of the two photodiodes, which is proportional to the output voltage of the device.

The voltage values measured are set out in the following table:

| DEGREE OF OXIDATION | DIFFERENCE (555 nm − 470 nm) in mV | | |
|---|---|---|---|
| in % | pH = 4.5 | pH = 5 | pH = 5.5 |
| 0 | 1.12 | 1.12 | 1.13 |
| 10 | 0.71 | 0.66 | 0.65 |
| 20 | 0.34 | 0.37 | 0.40 |
| 30 | 0.29 | 0.25 | 0.18 |
| 40 | 0.08 | 0.09 | 0.00 |
| 50 | 0.01 | 0.14 | 0.13 |

Figure 1B:
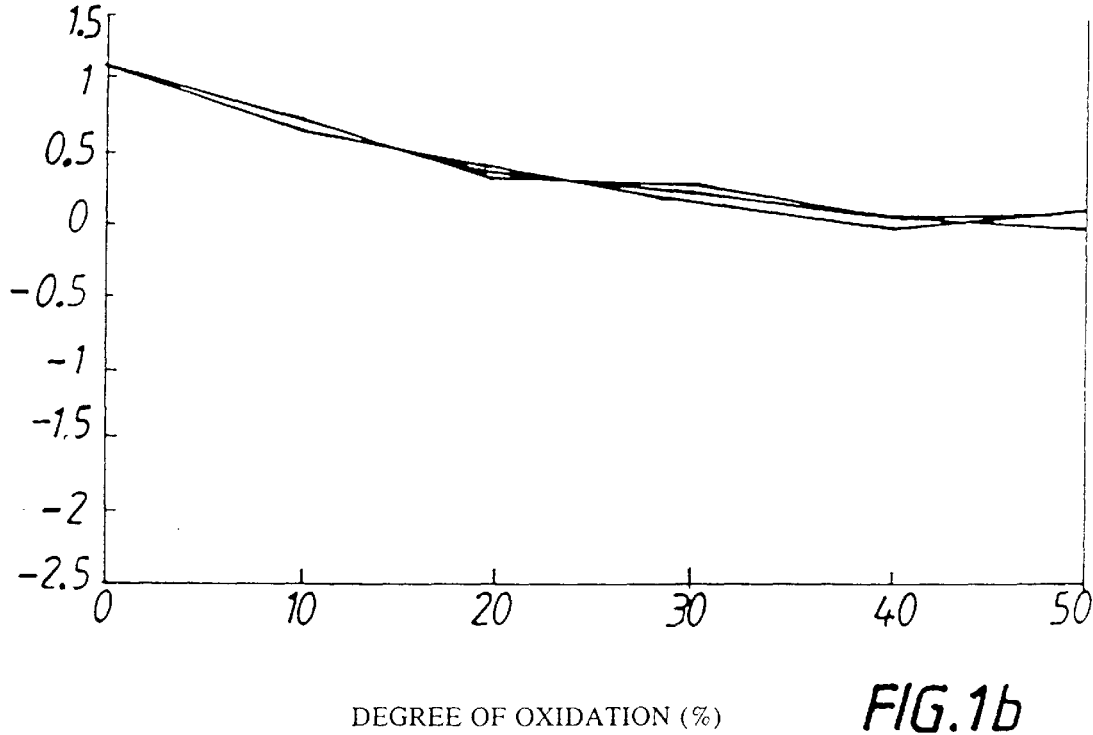
FIG. 1b depicts the voltage measurements as a function of the degree of oxidation for three different pH values.

These values are set out in FIG. 1b for the three pH values and on curve 3a for the composition with a pH of 4.5.

It is found first of all that the values measured do not vary with the pH.

It is noted in addition that the relationship between the optical density difference for the composition, which is proportional to the output voltage of the device, and the degree of oxidation of the complex, is monotonic. Thus it is possible to continuously monitor the degree of oxidation of the organometallic complex, and therefore the reducing activity of the development composition, by virtue of the optical density difference values measured.

The invention has been described in detail with particular reference to certain preferred embodiments thereof, but it will be understood that variations and modifications can be effected within the spirit and scope of the invention.

We claim:

1. A method of controlling the activity of a development composition which comprises, as a developing agent, an organometallic complex having at least one metallic ion capable of reducing the silver ions and at least one organic chelating agent, said composition also having an optical density that varies measurably as a function of the degree of oxidation of said organometallic complex, said method comprising measuring the optical density of said composition so as to determine the variation of the optical density related to the degree of oxidation of said organometallic complex and to eliminate the variations of the optical density which are not related to the variation of the degree of oxidation of said organometallic complex.

2. The method of claim 1 wherein said organometallic complex is a complex of titanium (III) with ethylenediaminetetraacetic acid (EDTA).

3. The method of claim 2, wherein said organometallic complex comprises, in addition to said EDTA chelating agent, at least one second organic chelating agent.

4. The method of claim 3, wherein said second organic complexing agent has the formula:

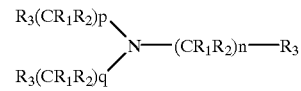

wherein $R^1$ and $R^2$ are each separately a hydrogen atom, an alkyl group, substituted or not, of 1 to 10 carbon atoms, a hydroxyl group, or a hydroxyalkyl group of 1 to 10 carbon atoms, and $R^3$ is —COOM in which M is hydrogen or a monovalent cation, —CONR$^4$R$^5$ wherein $R^4$ and $R^5$ are each separately a hydrogen atom, or an alkyl group, substituted or not, of 1 to 10 carbon atoms, and n, p and q are independently 1, 2 or 3.

5. The method of claim 4, wherein EDTA represents at least 25% by weight of the total organic chelating agents in said complex.

6. The method of claim 1 wherein a standard oxidoreduction potential control system is used conjointly.

7. A method of regenerating a development composition which comprises, as a developing agent, an organometallic complex having at least one metallic ion capable of reducing silver ions and at least one organic chelating agent, said composition also having an optical density that varies measurably with the degree of oxidation of said organometallic complex;

said method comprising:
a) measuring the optical density of said composition so as to determine the variation of the optical density related to the degree of oxidation of said organometallic complex and to eliminate the variations of the optical density which are not related to the variation of the degree of oxidation of said organometallic complex,
b) passing an electrolysis current through said composition, starting from a threshold value of optical density difference, thereby regenerating oxidized organometallic complex until the desired oxidation level is obtained.

* * * * *